United States Patent [19]

Eidt et al.

[11] 4,118,409

[45] Oct. 3, 1978

[54] PROCESS FOR THE SIMULTANEOUS PRODUCTION OF TRIMETHYLALUMINUM AND ALKYLALUMINUM HALIDES

[75] Inventors: Scott H. Eidt, Seabrook; Spencer C. Watson; George Charles Heilig, both of La Porte, all of Tex.

[73] Assignee: Texas Alkyls, Inc., Deer Park, Tex.

[21] Appl. No.: 455,448

[22] Filed: Mar. 27, 1974

[51] Int. Cl.$^2$ ............................................. C07F 5/06
[52] U.S. Cl. ............................................. 260/448 A
[58] Field of Search ............................................. 260/448 A

[56] References Cited

U.S. PATENT DOCUMENTS

| | | | |
|---|---|---|---|
| 2,691,668 | 10/1954 | Ziegler et al. | 260/448 A |
| 2,744,127 | 5/1956 | Ziegler et al. | 260/448 A |
| 2,786,860 | 3/1957 | Ziegler et al. | 260/448 A |
| 2,839,556 | 6/1958 | Ziegler et al. | 260/448 A |
| 2,863,894 | 12/1958 | Smith | 260/448 A |
| 2,931,820 | 4/1960 | Barclay et al. | 260/448 A |
| 2,952,698 | 9/1960 | Neal et al. | 260/448 A |

OTHER PUBLICATIONS

Mole et al., Organoaluminum Compounds, Elsevier Publ. Co., N.Y., pp. 10, 30 to 32 (1972).
Coates et al., Organometallic Compounds, Methuen & Co. Ltd., London, vol. 1, pp. 297–298 (1967).
Pitzer et al., J.A.C.S., 68, 2204 (1946).

*Primary Examiner*—Helen M. S. Sneed
*Attorney, Agent, or Firm*—Michael J. Bradley

[57] ABSTRACT

An economically attractive Redistribution Process for the production of trimethylaluminum and numerous alkylaluminum bromides and iodides is described herein. The Redistribution Process is a chemical reequilibration reaction which consists of forming a mixture of a methylaluminum bromide or iodide with aluminum trialkyl followed by separating by distillation, trimethylaluminum from the alkylaluminum bromides or iodides. The preferred method for separating the mixture of methylaluminum bromide or iodide and aluminum trialkyl into trimethylaluminum and alkylaluminum bromide or iodide is fractional distillation. Trimethylaluminum and the alkylaluminum bromides and iodides are valuable commercial materials for use as co-catalysts for the polymerization of various unsaturated hydrocarbons. Trimethylaluminum is also employed as a methylating agent, a chemical intermediate and a pyrophoric fuel.

13 Claims, No Drawings

PROCESS FOR THE SIMULTANEOUS PRODUCTION OF TRIMETHYLALUMINUM AND ALKYLALUMINUM HALIDES

BACKGROUND OF THE INVENTION

A number of processes exist in the prior art for production of trimethylaluminum, but each of these processes suffers from the disadvantage in that each yields by-products which are of little or no value and thus present disposal problems. U.S. Pat. No. 2,744,127 describes a relatively simple process for the preparation of trimethylaluminum which produces as a by-product magnesium chloride in the weight ratio 2.7:1 magnesium chloride: trimethylaluminum. The magnesium chloride has little or no commercial value.

Several processes have been developed by which trimethylaluminum is prepared by the sodium reduction of methylaluminum sesquichloride as described in British Patent No. 762,200 and U.S. Pat. No. 2,954,389 and in an article by A. V. Grosse and J. M. Mavity, *Journal of Organic Chemistry* 5, 106 (1940). Preparation of trimethylaluminum has also been carried out by the sodium reduction of dimethylaluminum chloride as described in an article by S. Pasynkiewicz and M. Boleslawski, *Journal of Organometallic Chemistry*, 25, 29 (1970). The methods described in the above articles each form a basis for existing commercial processes for the production of trimethylaluminum, but each produce non-useable by-products having limited value in vast quantities in comparison to the trimethylaluminum produced. The by-products produced by the above processes are aluminum and sodium chloride.

The several processes that have utilized the above sodium reduction reactions suffer from an inherent problem in that trimethylaluminum will itself react with sodium to produce sodium tetramethylaluminate, a compound that, unless it reacts with dimethylaluminum chloride, will cause reduced yields and present a a disposal problem. Sodium tetramethylaluminate is extremely reactive towards moisture in the air, as would excess unreacted sodium. The disposal problems presented by these two compounds would represent a significant proportion of the cost of production of trimethylaluminum manufactured by those processes.

Although the conversion of dimethylaluminum chloride to trimethylaluminum without the use of sodium (Cryolite Process) is described in U.S. Pat. No. 2,839,556, this reaction scheme produces a vast amount of solid by-product having limited commercial value.

Two other methods for production of aluminum trialkyls are described in an article by R. Köster and P. Binger, *Advances in Inorganic and Radiochemistry*, I 1263 (1965) and by K. S. Pitzer and H. S. Gutowsky, *Journal of American Chemical Society*, 68, 2204 (1946). Both of these methods suffer from the use of expensive starting materials and the production of non-useful or extremely reactive by-products requiring expensive process equipment and handling techniques.

BRIEF DESCRIPTION OF THE INVENTION

It has been discovered that trimethylaluminum and useful alkylaluminum bromides and iodides can be produced by a process that comprises mixing an aluminum trialkyl and a methylaluminum bromide or iodide and then distilling from said mixture trimethylaluminum as a first fraction and then alkylaluminum bromides or iodides as a subsequent fraction.

DETAILED DESCRIPTION OF THE INVENTION

The invention described herein is based upon a redistribution reaction involving organoaluminum compounds as the only reactants. For the sake of brevity, and in order to distinguish it from other methods for preparation of trimethylaluminum, the process is called the Redistribution Process.

The starting materials in the Redistribution Process are methylaluminum bromides or iodides and aluminum trialkyls in which the alkyl group is other than methyl. Preferably, the alkyl groups are primary alkyl radicals containing from 2 to about 16 carbon atoms. Aluminum trialkyls containing secondary or tertiary alkyl groups are not as preferred because these compounds are not as readily available or as stable as aluminum trialkyls made of primary alkyl radicals. Hereinafter halide means bromide or iodide and methylaluminum halide means dimethylaluminum halide, methylaluminum sesquihalide, methylaluminum dihalide or mixtures thereof.

Due to the fact that a principal objective of the invention is the production of a pure trimethylaluminum, methylaluminum bromides and iodides are preferred starting materials, while the methylaluminum chlorides, though less expensive, are not. The trimethylaluminum which is produced from methylaluminum chlorides is highly contaminated by dimethylaluminum chloride. The reason for this lies in the mechanism by which trimethylaluminum is produced. The redistribution reaction is a process of chemical reequilibration and chemical fractionation. Each distinct tray or plate in the fractionation column carries out the steps of fractionation, condensation and reequilibration as the more volitile trimethylaluminum is being formed and migrates to the end of the fractionation column furthest from the distillation pot. In the Redistribution Process, the immediate precursor to trimethylaluminum is the dimethylaluminum halide. Because trimethylaluminum and dimethylaluminum chloride have essentially the same boiling point, the two co-distill. On the other hand since trimethylaluminum is much more volatile than all dimethyl or dialkyl aluminum bromides or iodides, the pure trialkyl can be distilled from mixtures which contain these compounds.

Dependent upon the stoichiometry employed, the Redistribution Process can be used to prepare trimethylaluminum and alkylaluminum bromides or iodides such as dialkylaluminum bromides or iodides, alkylaluminum sesquibromides or iodides, alkylaluminum dibromides or diiodides or mixtures thereof. Equations illustrating the three different product combinations are shown below. For the purpose of illustration the methylaluminum halide in the equations is the methylaluminum sesquihalide. This material is used for two reasons. First, because the sesquihalide is an equimolar mixture of the dimethylaluminum halide and the methylaluminum dihalide, any reaction of the sesquihalide may be considered applicable to either compound. For example, by using the appropriate stoichiometry, a methylaluminum halide and an aluminum trialkyl can be mixed to produce trimethylaluminum and a dialkylaluminum halide, an alkylaluminum sesquihalide, or an alkylaluminum dihalide.

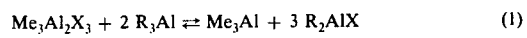

$$Me_3Al_2X_3 + 2 R_3Al \rightleftarrows Me_3Al + 3 R_2AlX \qquad (1)$$

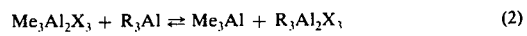

$$Me_3Al_2X_3 + R_3Al \rightleftarrows Me_3Al + R_3Al_2X_3 \qquad (2)$$

$$2 \text{Me}_3\text{Al}_2\text{X}_3 + \text{R}_3\text{Al} \rightleftarrows 2 \text{Me}_3\text{Al} + 3 \text{RAlX}_2 \qquad (3)$$

(wherein X = bromide or iodide in all equations herein and R = alkyl as defined above). A second reason for emphasizing the methylaluminum sesquihalide as a starting material is that these species are the cheapest and most readily prepared methylaluminum compounds. Methylaluminum sesquihalides are produced by the facile reaction between aluminum metal and methyl halides, both of which are available as industrial chemicals.

There are several factors which influence the choice of conditions used in the Redistribution Process. The desired alkylaluminum halide determines the aluminum trialkyl, the methylaluminum sesquihalide, and to a large extent, the molar ratio of the two reactants. Other factors which are influential include the purity of the aluminum trialkyl starting material and the contaminants, if any, which can be tolerated in the trimethylaluminum. While most impurities in the aluminum trialkyl starting material do not subsequently appear in the trimethylaluminum, some are capable of producing a compound which is not readily separable from trimethylaluminum. The compound, dimethylaluminum hydride, has a boiling point (154° C.) which is significantly higher than that of trimethylaluminum. However, the two compounds form azeotropic mixtures or stable mixed dimer complexes that distill at temperatures slightly below the trimethylaluminum boiling point. Thus, the dialkylaluminum hydride which is present as an impurity in the aluminum trialkyl starting material can react, as shown by Equation 4, to form dimethylaluminum hydride.

$$\text{R}_2\text{AlH} + \text{Me}_2\text{AlX} \rightleftarrows \text{Me}_2\text{AlH} + \text{R}_2\text{AlX} \qquad (4)$$

Therefore, one way to minimize the hydride content of trimethylaluminum involves the use of an aluminum trialkyl starting material that contains a low percentage dialkylaluminum hydride. Another way is to employ reaction conditions whereby the dialkylaluminum hydride is converted to a compound other than dimethylaluminum hydride. The compound, aluminum trihydride, is formed by the reaction shown in Equation (5). At temperatures higher than 80° C. aluminum trihydride decomposes into the two elements.

$$3 \text{R}_2\text{AlH} + 2 \text{RAlX}_2 \rightleftarrows 4 \text{R}_2\text{AlX} + \text{AlH}_3 \qquad (5)$$

$$2 \text{AlH}_3 \rightleftarrows 2 \text{Al} + 3 \text{H}_2 \qquad (6)$$

Neither the aluminum nor the hydrogen is reactive with the organoaluminum compounds, and neither is soluble in the mixture. As shown by Equation (5), an alkylaluminum dihalide is the reactant responsible for the conversion of the dialkylaluminum hydride to aluminum trihydride. The alkylaluminum dibromide or diiodide may be a methylaluminum dihalide or one derived from the aluminum trialkyl starting material. In order that a mixture of aluminum alkyls have an effective concentration of alkylaluminum dihalide to react with the dialkylaluminum hydride, the mixtures must have an atomic ratio, halogen/aluminum, which is at least 1.0 or greater. Of the three mixtures shown in Equations 1-3, the last two have atomic ratios of halogen/aluminum that permit the presence of alkylaluminum dihalide. In the first mixture, wherein the atomic ratio halogen/aluminum ratio is 0.75, there is no alkylaluminum dihalide available for reaction with the dialkylaluminum hydride. Several factors determine the halogen/aluminum ratio that would be optimum for a particular preparation. The stoichiometric relationship that determines the type of alkylaluminum halide (see Equations 1-3 above) also determines the halogen/aluminum ratio of the mixture. The halogen/aluminum ratio for Equations 1-3 are respectively 0.75, 1.0 and 1.2. The preferred halogen/aluminum ratio is from about 0.6 to about 1.50 as dictated by stoichiometry depending on the alkylaluminum halide by-products desired. As a result, the alkylaluminum halide produced can be monoalkylaluminum dihalide, a dialkylaluminum monohalide, an alkylaluminum sesquihalide or mixture of the above three alkylaluminum compounds.

The hydride content of the trimethylaluminum is influenced by the halogen/aluminum ratio if the $\text{R}_3\text{Al}$ starting material either contains a significant concentration of $\text{R}_2\text{AlH}$, or is of a type that undergoes appreciable thermal decomposition to $\text{R}_2\text{AlH}$ + olefin during the distillation. If it is acceptable that the trimethylaluminum contain a moderately high percentage $\text{Me}_2\text{AlH}$, the following conditions could be employed:

1. Use of an aluminum trialkyl containing a high $\text{R}_2\text{AlH}$ content.
2. Use of an aluminum trialkyl that will undergo partial decomposition to $\text{R}_2\text{AlH}$ + olefin during the distillation of the trimethylaluminum.
3. Use of a reaction mixture in which the initial halogen/aluminum is <1.0, i.e., one which contains no $\text{RAlX}_2$.

Conversely, trimethylaluminum having a low hydride content is obtained by employing the following conditions:

1. Use of an aluminum trialkyl containing little or no hydride.
2. Use of an aluminum trialkyl that is resistant to decomposition to $\text{R}_2\text{AlH}$ + olefin during the distillation of trimethylaluminum.
3. Use of a reaction mixture wherein the initial halogen/aluminum is 1.0 or >1.0, i.e., one that contains a significant concentration of $\text{RAlX}_2$.

The temperature range for the Redistribution Process is that in the system during the distillation of trimethylaluminum, i.e., ranging from the low temperature in the vapor to the high temperature of the liquid in the still pot. The distillation temperature and pressure can range from 15.3° C. at 7 Torr to at least 126°-127° C. at atmospheric pressure. The trimethylaluminum even can be distilled at superatmospheric pressure and resultant higher temperatures without significant decomposition of the trimethylaluminum, but some decomposition of the other alkylaluminum compounds may occur because of high pot temperatures. The preferred range is from 20-300 Torr with distillation temperature dependent thereon. The vapor temperature, i.e., the boiling point of trimethylaluminum, is determined by the pressure employed in the distillation. At the most preferred employed pressures, those in the range 50-150 Torr, the boiling point range of trimethylaluminum is 53°-78° C. Distillation at the higher pressures provides a greater differential between the boiling point and the condenser temperature. When the latter is significantly lower than 15° C., the freezing point of trimethylaluminum, the likelihood of plugging the condenser with frozen distillate is great. Though the temperature of the trimethylaluminum vapor remains essentially unchanged throughout a distillation carried out at constant pressure, the pot liquid temperature gradually increases due to the increase in concentration of the higher boiling components. Pot temperatures in the vicinity of 200° C. are common in the latter stages of a distillation of trimethylaluminum.

The initial step in the Redistribution Process consists of the mixing of the aluminum trialkyl and methylaluminum halide in a reaction vessel containing an inert atmosphere. The vessel may be the distillation still pot used in the next step. The aluminum trialkyl may be added to previously prepared methylaluminum halide, or the latter may be prepared in the presence of the aluminum trialkyl. In the latter case, the methyl bromide or iodide is charged to a stirred suspension of activated aluminum in the aluminum trialkyl. The heat generated by this reaction, which is normally carried out at slight super-atmospheric pressures, is much greater than that produced by mixing the aluminum trialkyl and previously prepared methylaluminum halide. Under the conditions of the Redistribution Process, no readily detectable reaction occurs between the methyl bromide or iodide and the aluminum trialkyl.

In the second step, the redistribution reaction proceeds in a practical manner. An efficient fractionating column provides the conditions which promote the Redistribution Process. An efficient fractional distillation column is defined as a column capable of distilling pure trimethylaluminum from a mixture composed of trimethylaluminum and an alkylaluminum halide having a boiling point at atmospheric pressure that is higher than 150° C. Examples of such an efficient column are a packed column, a bubble captray column and a spinning band column. In the upper portions of the column, where the more volatile dimethylaluminum halide is concentrated, the environment favors the formation of trimethylaluminum. Being much more volatile than the dimethylaluminum halide, trimethylaluminum escapes the liquid surface and is no longer subject to redistribution. Trimethylaluminum that is free of dimethylaluminum halide can be obtained by using an efficient column and a high reflux ratio. The yield of trimethylaluminum is in the range 80–95% of theory.

After the removal of the bromide or iodide-free trimethylaluminum fraction, a small intermediate fraction is distilled. This fraction, primarily a mixture of trimethylaluminum and dimethylaluminum halide, contains the majority of the methyl groups which remained after the distillation of the pure trimethylaluminum. In a commercial process this fraction would be recycled.

The residual still pot liquid has a low methylaluminum content. Also, the residue contains substantially all the alkyl groups from the aluminum trialkyl originally charged, and with the exception of that distilled in the intermediate fraction, all the bromide or iodide which was present in the methylaluminum halide charge. Thus, dependent upon the molar ratio of aluminum trialkyl to methylaluminum halide used, the residual still pot liquid is substantially pure dialkylaluminum halide, alkylaluminum sesquihalide, or alkylaluminum dihalide. Most of these compounds are liquids, while some are solids that have melting points slightly higher than ambient temperature. Though all are significantly less volatile than the methylaluminum halides, some have boiling points at subatmospheric pressures which are sufficiently low to permit distillation without decomposition.

The process described in this invention possesses distinct advantages over other processes for the production of trimethylaluminum. One advantage is the simplicity of the process equipment used. Because the reactants and products are compounds which are liquid at ambient or slightly above ambient temperature, these materials are easily transferred, via piping or tubing, from one vessel to another. The reaction vessels do not require the powerful, efficient and expensive agitators which are necessary in processes wherein a reactant and/or reaction product are solids. No expensive or complex filtration apparatus or other solids-handling equipment is necessary. Most other processes for the preparation of trimethylaluminum use less expensive starting materials than the aluminum trialkyl and the methylaluminum halide required in the Redistribution Process, but, the other processes yield trimethylaluminum as the only product of significant value, while the Redistribution Process produces not only trimethylaluminum, but alkylaluminum halides which are valuable commercial products.

The above described invention can be further understood by the following specific examples.

EXAMPLE 1

The reaction vessel-still pot was a 1-liter, 2-necked flask containing a magnetic stirrer bar and built-in thermowell. Fitted on the flask were an additional funnel and a distillation column having $\frac{3}{4}''$ i.d. and packed with 24" of small, stainless steel protruded packing. Atop the column was a variable reflux ratio distillation head which contained efficient reflux and distillation condensers. Through these condensers was a rapid flow of a silicone heat exchange fluid having a temperature of 15° C. As a receiver for the distillate, a 300 ml flask was connected to the lower end of the distillation condenser.

After the system had been thoroughly dried and purged with dry, high-purity nitrogen, the reaction flask was charged with 84 g (3.1 gram atoms) of finely divided aluminum having a purity greater than 99.5%w and a very low oxide content. Atop the aluminum was added 320 g (2.80 moles) of triethylaluminum having a hydride content lower than 0.3%w calculated as $AlH_3$. The stirred slurry was heated to 60° C., the heat was removed, and the dropwise addition of mole sieve-dried methyl iodide was begun. During a six-hour addition period, while the temperature of the reaction mixture was in the range 60°–80° C., 596 g (4.20 moles) of methyl iodide were charged to the stirred mixture. Upon completion of the addition of methyl iodide, the mixture was heated to 100° C. and held at this temperature for ½ hour to insure completion of reaction of the aluminum and methyl iodide. Because an excess of aluminum was used, the final mixture contained black, unreacted aluminum.

Preparatory to distillation, vacuum was slowly applied to the system until the pressure had decreased to 100 Torr. With the pressure constant at 100 Torr, the reaction flask-still pot was heated until trimethylaluminum began to reflux. Later, as distillation progressed, the pot temperatures was gradually increased in order to maintain a practical reflux rate. During the distillation, which began at reflux ratio of 4 and ended at 10, there distilled 91 g of trimethylaluminum boiling in the range 65°–68° C. Based upon methyl iodide and triethylaluminum as limiting reactants, the weight of distillate represented a 90% yield of trimethylaluminum. The distillate contained no iodide-containing compound and had a hydride content calculated as 0.8%w $AlH_3$.

A second fraction of distillate, 9 g boiling in the range 104°-109° C. at 100 Torr, was collected at a reflux ratio of 10. This fraction, which consisted of 20%w trimethylaluminum, 57%w dimethylaluminum iodide and 23%w triethylaluminum, was distilled in order to reduce the methylaluminum content of the still pot liquid.

The residual liquid in the still pot was distilled through a short Vigreaux column. Boiling in the range 111°-121° C. at 10 Torr, there distilled 840 g of liquid. This weight represented a 94% yield of diethylaluminum iodide. Analysis indicated the distillate consisted of 98%w diethylaluminum iodide, with the principal impurity being 1%w dimethylaluminum iodide.

EXAMPLE 2

This example illustrates the preparation of trimethylaluminum and ethylaluminum diiodide. The reaction and the distillation of trimethylaluminum were carried out in the same equipment as used in Example 1. While the triethylaluminum used was of the same type as that in Example 1, previously prepared methylaluminum sesquiiodide was employed as a starting material instead of carrying out the reaction of methyl iodide with aluminum in triethylaluminum. Thus, to 1,439 g (3.0 moles) of methylaluminum sesquiiodide stirred at 50°-60° C. were added 171 g (1.5 moles) of triethylaluminum in a 10 minute period. A slight exotherm occurred during this operation.

Following adjustment of the pressure in the system from atmospheric to 100 Torr, and then heating the mixture until a constant reflux temperature was obtained, trimethylaluminum was distilled at a reflux ratio of 10. At the vapor temperature of 69° C. there distilled 196 g of liquid; representing 91% of the theoretical yield of trimethylaluminum. Analysis of the distillate revealed no iodide and a hydride content equivalent to 0.1%w AlH$_3$.

Because complete distillation of all the methylaluminum groups as pure trimethylaluminum is not possible, and, in order to reduce the methylaluminum content of the still pot liquid to a low level, a fraction consisting of trimethylaluminum and dimethylaluminum iodide was distilled. There were collected at the reflux ratio of 4, 21 g of distillate boiling in the range 34°-68° C. at 70 Torr. Remaining in the still pot was 1,355 g of liquid which crystallized upon standing at ambient temperature. The weight represented a 97% yield of crude ethylaluminum diiodide. The principal impurities were 2.3%w methylaluminum diiodide and 1.1%w n-butylaluminum diiodide.

The distillation flask containing the crude ethylaluminum diiodide was removed from the packed fractionating column and connected to a short-path column-head-condenser system where the product was purified by flash distillation. At 0.2 Torr, there distilled 1,315 g of distillate boiling in the range 101°-106° C. A white crystalline solid at ambient temperature, the product melted at 35° C. Analysis indicated a 97.3%w ethylaluminum diiodide content, with the principal impurity being 2.1%w methylaluminum diiodide.

EXAMPLE 3

This example demonstrates the necessity of employing an efficient fractionating column in the preparation of trimethylaluminum via the Redistribution Process. The reaction mixture in the experiment was prepared in the same manner as that in Example 2, i.e., by adding 1.5 moles of triethylaluminum to 3.0 moles of methylaluminum sesquiiodide. This mixing was carried out in a 1-liter flask fitted with a 24" vacuum-jacketed Vigreaux column atop which was a variable reflux ratio distillation head. After the pressure in the system was adjusted to 100 Torr, the liquid was heated until a rapid reflux was obtained at a constant vapor temperature of 79° C. Then, at vapor temperatures in the range 79°-81° C., 12 g of distillate were distilled. This distillate, having a boiling temperature approximately 11° C. higher than the bp of trimethylaluminum, was analyzed and found to be trimethylaluminum contaminated by dimethylaluminum iodide and compounds containing the ethylaluminum group. The distillate was returned to the still pot and the Vigreaux column was replaced by a vacuum-jacketed distillation column having a 3/4" × 24" section filled with stainless steel protruded packing. Then, through the same distillation head as used with the Vigreaux column, at 69° C. and 100 Torr there distilled 192 g of liquid, corresponding to an 89% yield of trimethylaluminum. This distillate, unlike that obtained using the Vigreaux column, contained no compound having an aluminum-iodide bond or ethylaluminum group. Thus, a Vigreaux column, which has little fractionating efficiency as compared with a packed column, cannot be used in the Redistribution Process.

EXAMPLE 4

This example describes the preparation of trimethylaluminum and diethylaluminum bromide from methylaluminum sesquibromide and triethylaluminum. The equipment used, which was the same as in Example 1, was thoroughly dried and purged with dry, high-purity nitrogen prior to being charged with the air and moisture-sensitive reactants.

To 508 g (1.5 moles) of methylaluminum sesquibromide stirred at 50°-60° C. were charged 342 g (3.0 moles) of triethylaluminum in a 10-minute period. The temperature of the reaction mixture increased approximately 30° C. during the addition, and then began to decrease after the addition was complete. With the liquid temperature initially below 60° C., the pressure in the system was reduced from atmospheric to 100 Torr and maintained constant at this level during the subsequent distillation. The still pot was heated until, at 65° C. in the vapor, refluxing began in the distillation head. Distillation was started at a reflux ratio of 4 and completed at 20. In order to maintain a high reflux rate, the pot temperature was gradually raised throughout the distillation. At 100 Torr trimethylaluminum distilled in the temperature range 65°-68° C. The 95 g of distillate corresponded to 88% of the theoretical quantity of trimethylaluminum. Analysis revealed no bromine-containing compound in the distillate. The hydride value was equivalent to a 0.7%w AlH$_3$ content.

An intermediate fraction of distillate boiling in the range 52°-88° C. at 50 Torr was collected using a reflux ratio of 20. The 22 g of distillate consisted of 25%w trimethylaluminum, 20%w triethylaluminum and 55%w dimethylaluminum bromide. As in Examples 1 and 2, the intermediate fraction was distilled to reduce the methylaluminum content of the residual liquid in the still pot. This liquid was subsequently distilled through a Vigreaux column. In the range 147°-148° C. at 50 Torr there distilled 708 g of diethylaluminum bromide, corresponding to a 95% yield.

EXAMPLE 5

In this example is described the preparation of trimethylaluminum and n-butylaluminum dibromide. The equipment used in the reaction step and in the distillation of fractions which contained trimethylaluminum was the same as used in Example 1.

The reaction mixture that was prepared by the addition of 198 g (1.0 moles) of tri-n-butylaluminum to 678 g (2.0 moles) of methylaluminum sesquibromide was subjected to fractional distillation at 100 Torr. After fractionation of 125 g of bromidefree trimethylaluminum, corresponding to an 87% yield, there were distilled 27 g of a mixture of trimethylaluminum and dimethylaluminum bromide. Analysis indicated the still pot residue consisted of 2.8%w methylaluminum dibromide and 97.2%w n-butylaluminum dibromide. The still pot was removed from the fractional distillation column and installed in a distillation system which contained a short Vigreaux column. Following the flash vacuum distillation of 20 g of methylaluminum dibromide, there remained a 692 g still pot residue, corresponding to a 94.6% yield of n-butylaluminum dibromide.

EXAMPLE 6

The attempted preparation of trimethylaluminum and diethylaluminum chloride from methylaluminum sesquichloride and triethylaluminum was carried out in the same equipment as used in Example 1. A mixture prepared from 205 g (0.1 moles) of methylaluminum sesquichloride and 228 g (2.0 moles) of triethylaluminum was the still pot charge in the distillation. Employing a reflux ratio of 20 and a pressure of 100 Torr, 78 g of distillate boiling in the range 65°–68° C. were collected. Analysis revealed the distillate to consist of 79%w dimethylaluminum chloride and 21%w trimethylaluminum. Subsequent fractions of distillate were complex mixtures of methylaluminum chlorides, ethylaluminum chlorides and triethylaluminum.

Though no pure trimethylaluminum was obtained, the initial fraction of distillate did contain a significant amount of trimethylaluminum along with the major component, dimethylaluminum chloride. This result contrasts with that obtained upon distillation of methylaluminum sesquichloride in the absence of triethylaluminum. Under fractional distillation conditions, methylaluminum sesquichloride by itself does not disproportionate to a fraction consisting of trimethylaluminum and dimethylaluminum chloride and a residue composed of methylaluminum dichloride and aluminum trichloride.

What is claimed is:

1. A Redistribution Process for the production of trimethylaluminum and alkylaluminum bromides or iodides comprising forming a mixture of methylaluminum halides selected from the group consisting of dimethylaluminum bromide, dimethylaluminum iodide, methylaluminum dibromide, methylaluminum diiodide, methylaluminum sesquibromide, methylaluminum sesquiiodide, a mixture of dimethylaluminum bromide, methylaluminum dibromide and methylaluminum sesquibromide and a mixture of dimethylaluminum iodide, methylaluminum diiodide and methylaluminum sesquiiodide and an aluminum trialkyl wherein the alkyl radicals contain from 2 to about 16 carbon atoms and distilling said mixture in an efficient distillation column to effect separation of said mixture into a first fraction consisting essentially of trimethylaluminum and a residue of alkylaluminum bromides or iodides.

2. The process of claim 1 in which the alkyl groups of the aluminum trialkyl consist of primary alkyl radicals containing from 2 to about 16 carbon atoms.

3. The process of claim 1 in which the halogen/aluminum ratio of the mixture is from about 0.6 to about 1.5.

4. The process of claim 1 in which the methylaluminum halide is selected from the group of methylaluminum dibromide, dimethylaluminum bromide, methylaluminum sesquibromide and mixtures of methylaluminum dibromide, dimethylaluminum bromide and methylaluminum sesquibromide.

5. The process of claim 1 in which the methylaluminum halide is methylaluminum dibromide.

6. The process of claim 1 in which the methylaluminum halide is dimethylaluminum bromide.

7. The process of claim 1 in which the methylaluminum halide is methylaluminum sesquibromide.

8. The process of claim 1 in which the methylaluminum halide is a mixture of methylaluminum dibromide, dimethylaluminum bromide and methylaluminum sesquibromide.

9. The process of claim 1 in which the methylaluminum halide is selected from the group of methylaluminum diiodide, dimethylaluminum iodide, methylaluminum sesquiiodide, and mixtures of methylaluminum diiodide, dimethylaluminum iodide and methylaluminum sesquiiodide.

10. The process of claim 1 in which the methylaluminum halide is methylaluminum diiodide.

11. The process of claim 1 in which the methylaluminum halide is methylaluminum iodide.

12. The process of claim 1 in which the methylaluminum halide is methylaluminum sesquiiodide.

13. The process of claim 1 in which the methylaluminum halide is a mixture of methylaluminum diiodide, dimethylaluminum iodide and methylaluminum sesquiiodide.

* * * * *

UNITED STATES PATENT AND TRADEMARK OFFICE
CERTIFICATE OF CORRECTION

PATENT NO. : 4,118,409
DATED : October 3, 1978
INVENTOR(S) : Scott H. Eidt et al.

It is certified that error appears in the above-identified patent and that said Letters Patent are hereby corrected as shown below:

Column 9, line 30, (0.1 moles) should read (1.0 moles).

Column 10, Claim 11, line 48, methylaluminum iodide should read dimethylaluminum iodide.

Column 4, line 54, the word "pressure" should be inserted between preferred and range.

Signed and Sealed this

Eighteenth Day of September 1979

[SEAL]

Attest:

LUTRELLE F. PARKER
Attesting Officer    Acting Commissioner of Patents and Trademarks